(12) United States Patent
Williams et al.

(10) Patent No.: US 7,712,802 B2
(45) Date of Patent: May 11, 2010

(54) CASSETTE CLAMPING MECHANISM

(75) Inventors: David L. Williams, Newport Beach, CA (US); Michael Bowman, Fullerton, CA (US)

(73) Assignee: Alcon, Inc., Hunenberg (CH)

( * ) Notice: Subject to any disclaimer, the term of this patent is extended or adjusted under 35 U.S.C. 154(b) by 1001 days.

(21) Appl. No.: 11/451,050

(22) Filed: Jun. 12, 2006

(65) Prior Publication Data

US 2007/0286755 A1 Dec. 13, 2007

(51) Int. Cl.
B65D 45/00 (2006.01)

(52) U.S. Cl. ................................ 292/256; 292/257

(58) Field of Classification Search ............... 292/256, 292/257, 256.65, 256.69, 256.75, 261
See application file for complete search history.

(56) References Cited

U.S. PATENT DOCUMENTS

| | | | |
|---|---|---|---|
| 3,756,752 A | 9/1973 | Stenner | |
| 4,256,442 A | 3/1981 | Lamadrid et al. | |
| 4,395,258 A | 7/1983 | Wang et al. | |
| 4,493,695 A | 1/1985 | Cook | |
| 4,626,248 A | 12/1986 | Scheller | |
| 4,627,833 A | 12/1986 | Cook | |
| 4,713,051 A | 12/1987 | Steppe et al. | |
| 4,758,220 A | 7/1988 | Sundblom et al. | |
| 4,758,238 A | 7/1988 | Sundblom et al. | |
| 4,790,816 A | 12/1988 | Sundblom et al. | |
| 4,798,580 A | 1/1989 | DeMeo et al. | |
| 4,798,850 A | 1/1989 | Brown | |
| 4,824,339 A | 4/1989 | Bainbridge et al. | |
| 4,904,168 A | 2/1990 | Cavoto et al. | |
| 4,927,411 A | 5/1990 | Pastrone et al. | |
| 5,125,891 A | 6/1992 | Hossain et al. | |
| 5,195,960 A | 3/1993 | Hossain et al. | |
| 5,230,614 A | 7/1993 | Zanger et al. | |
| 5,267,956 A | 12/1993 | Beuchat et al. | |
| 5,324,180 A | 6/1994 | Zanger | |
| 5,330,331 A * | 7/1994 | Doede ......................... 417/519 |
| 5,364,342 A | 11/1994 | Beuchat et al. | |
| 5,387,088 A | 2/1995 | Knapp et al. | |
| 5,417,395 A | 5/1995 | Fowler et al. | |
| 5,445,506 A | 8/1995 | Afflerbaugh et al. | |
| 5,588,815 A | 12/1996 | Zaleski, II | |
| 5,676,530 A | 10/1997 | Nazarifar | |
| 5,810,770 A | 9/1998 | Chin et al. | |
| 6,036,458 A | 3/2000 | Cole | |
| 6,053,543 A | 4/2000 | Arabia et al. | |

(Continued)

FOREIGN PATENT DOCUMENTS

AU 703803 7/1997

(Continued)

OTHER PUBLICATIONS

European Patent Office, European Search Report, EP 07 10 9823, Sep. 6, 2007, (2 pages).

*Primary Examiner*—Peter M. Cuomo
*Assistant Examiner*—Mark Williams

(57) ABSTRACT

A mechanism having a pair of pivoting cassette clamping bars. The clamping bars are connected to a pneumatic cylinder or an electromechanical actuator through a series of links and an actuator wheel so that extension and retraction of the pneumatic cylinder or the electromechanical actuator causes the clamping bars to rotate and counter-rotate. The use of a pneumatic cylinder provides smooth, well-controlled movement of the clamping bars.

10 Claims, 7 Drawing Sheets

U.S. PATENT DOCUMENTS

| | | | |
|---|---|---|---|
| 6,059,544 | A | 5/2000 | Jung |
| 6,059,765 | A | 5/2000 | Cole et al. |
| 6,076,868 | A | 6/2000 | Roger, Jr. et al. |
| 6,101,406 | A | 8/2000 | Hacker et al. |
| 6,267,956 | B1 | 7/2001 | Gomes |
| 6,272,833 | B1 * | 8/2001 | Stephan ............. 57/281 |
| 6,293,926 | B1 | 9/2001 | Sorensen et al. |
| 6,302,455 | B1 | 10/2001 | Huang |
| 6,364,342 | B1 | 4/2002 | Kim |
| 7,070,578 | B2 * | 7/2006 | Leukanech et al. ......... 604/153 |
| 2001/0016711 | A1 | 8/2001 | Sorensen et al. |
| 2003/0202894 | A1 * | 10/2003 | Leukanech et al. ....... 417/477.2 |
| 2003/0204172 | A1 | 10/2003 | Steppe |
| 2003/0225363 | A1 | 12/2003 | Gordon |
| 2004/0074281 | A1 | 4/2004 | Lobdell et al. |
| 2004/0106915 | A1 | 6/2004 | Thoe |
| 2004/0253129 | A1 | 12/2004 | Sorensen |
| 2005/0065462 | A1 | 3/2005 | Nazarifar |
| 2005/0186098 | A1 | 8/2005 | Davis |
| 2005/0234395 | A1 | 10/2005 | Mackool |
| 2005/0285025 | A1 | 12/2005 | Boukhny et al. |
| 2007/0252395 | A1 | 11/2007 | Williams et al. |
| 2008/0015515 | A1 | 1/2008 | Hopkins |

FOREIGN PATENT DOCUMENTS

| | | |
|---|---|---|
| EP | 0786260 B1 | 7/1997 |
| EP | 1366776 A1 | 3/2003 |
| EP | 1356835 A1 | 10/2003 |
| EP | 1849488 A1 | 10/2007 |
| EP | 1867349 A1 | 12/2007 |
| EP | 1872810 A1 | 1/2008 |
| GB | 2051455 | 5/1979 |
| JP | 2003-319964 | 11/2003 |
| JP | 2005-016057 | 1/2005 |

* cited by examiner

CASSETTE CLAMPING MECHANISM

BACKGROUND OF THE INVENTION

The present invention relates generally to peristaltic pumps and more specifically to clamping mechanisms for use on ophthalmic surgical equipment fluidic cassettes.

Most prior art peristaltic pumps work by compressing or squeezing a length of flexible tubing (sometimes between a fixed race) using a rotating roller head. As the roller head rotates, the rollers pinch off a portion of the tubing and push any fluid trapped in the tubing between the rollers in the direction of rotation. Peristaltic pumps are widely used in medical applications because of their predictable, constant flow properties. These prior art systems, however, typically require manual connection of the pump tube segment around the rotating roller head.

Another prior art pump is disclosed in U.S. Pat. No. 6,293,926 B1 (Sorensen, et al.) which describes a peristaltic pump having a molded flow channel contained on an elastomeric sheet that is bonded or mechanically attached to a rigid substrate. The pump head rollers are mounted radially from the axis of rotation of the pump motor and compress the elastomeric flow channels against the rigid substrate. In order to fully compress the flow channels against the rigid substrate, and thereby maximize the efficiency of the pumping system, the cassette must be held tightly against the pump rollers. The cassette, on the other hand, must also be easy to install on and be removed from the surgical console. One cassette latching mechanism, disclosed in U.S. Patent Publication No. 20030202894 (Leukanech, et al.), discloses a cassette latching mechanism having a motor that rotates a latching wheel, producing cam-like movement of a pair of latching arms and thereby pivoting the latching rails to a fully closed and locked position holding the cassette. The DC servo motors used in this device are expensive and can be relatively abrupt in operation.

Accordingly, a need continues to exist for an inexpensive cassette clamping having smooth, controlled movement.

BRIEF SUMMARY OF THE INVENTION

The present invention improves upon prior art cassette clamping mechanisms by providing a mechanism having a pair of pivoting cassette clamping bars. The clamping bars are connected to a pneumatic cylinder or an electromechanical actuator through a series of links and an actuator wheel so that extension and retraction of the pneumatic cylinder or the electromechanical actuator causes the clamping bars to rotate and counter-rotate. The use of a pneumatic cylinder provides smooth, well-controlled movement of the clamping bars.

Accordingly, one objective of the present invention is to provide a cassette clamping mechanism.

Another objective of the present invention is to provide a pneumatically controlled cassette clamping mechanism.

Another objective of the present invention is to provide a cassette clamping mechanism having smooth, controlled movement.

Yet another objective of the present invention is to provide a relatively inexpensive cassette clamping mechanism.

Yet another objective of the present invention is to provide a relatively high-force and long-stroke mechanism in a small envelope size.

These and other advantages and objectives of the present invention will become apparent from the detailed description, drawings and claims that follow.

DETAILED DESCRIPTION OF THE PREFERRED EMBODIMENT

Figure 1:
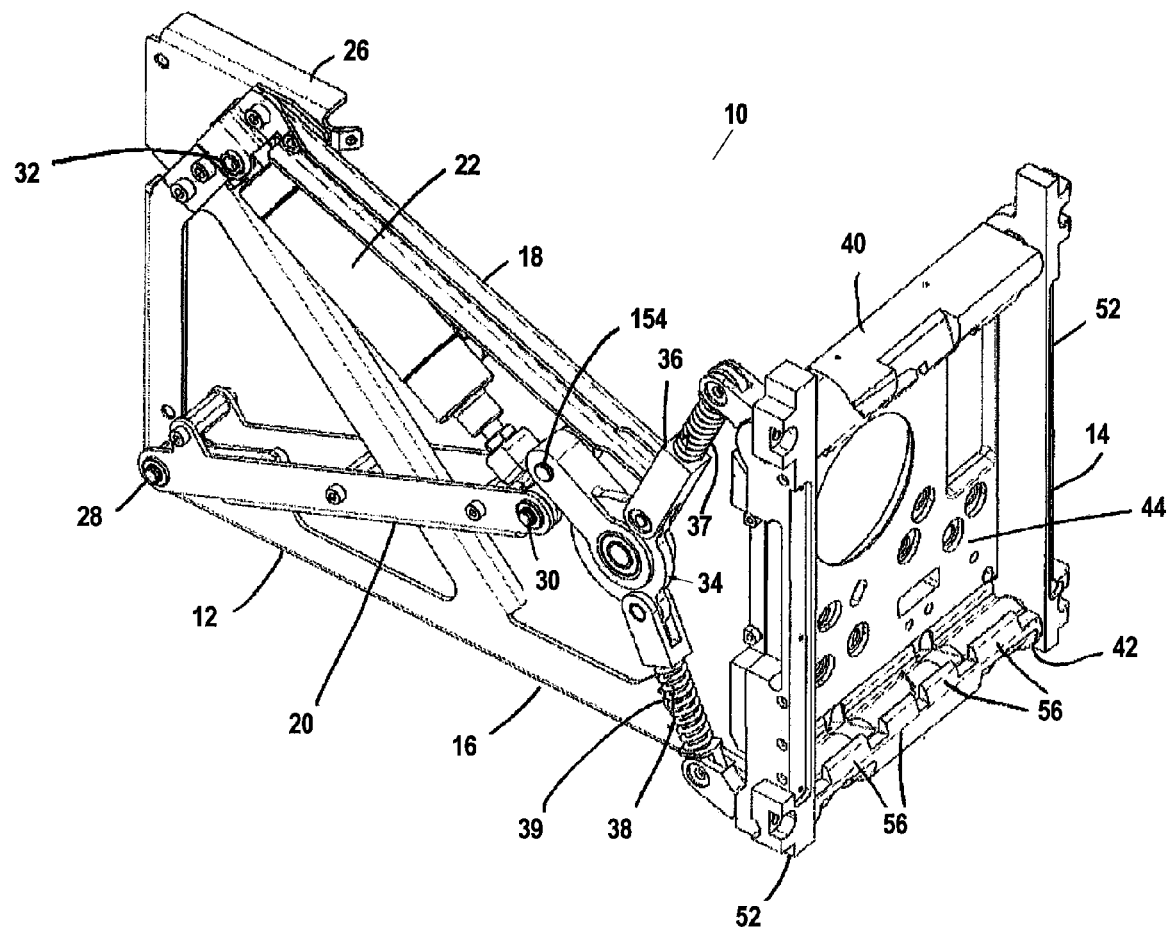
FIG. 1 is a front perspective view of the cassette clamping mechanism assembly of the present invention.
Figure 2:
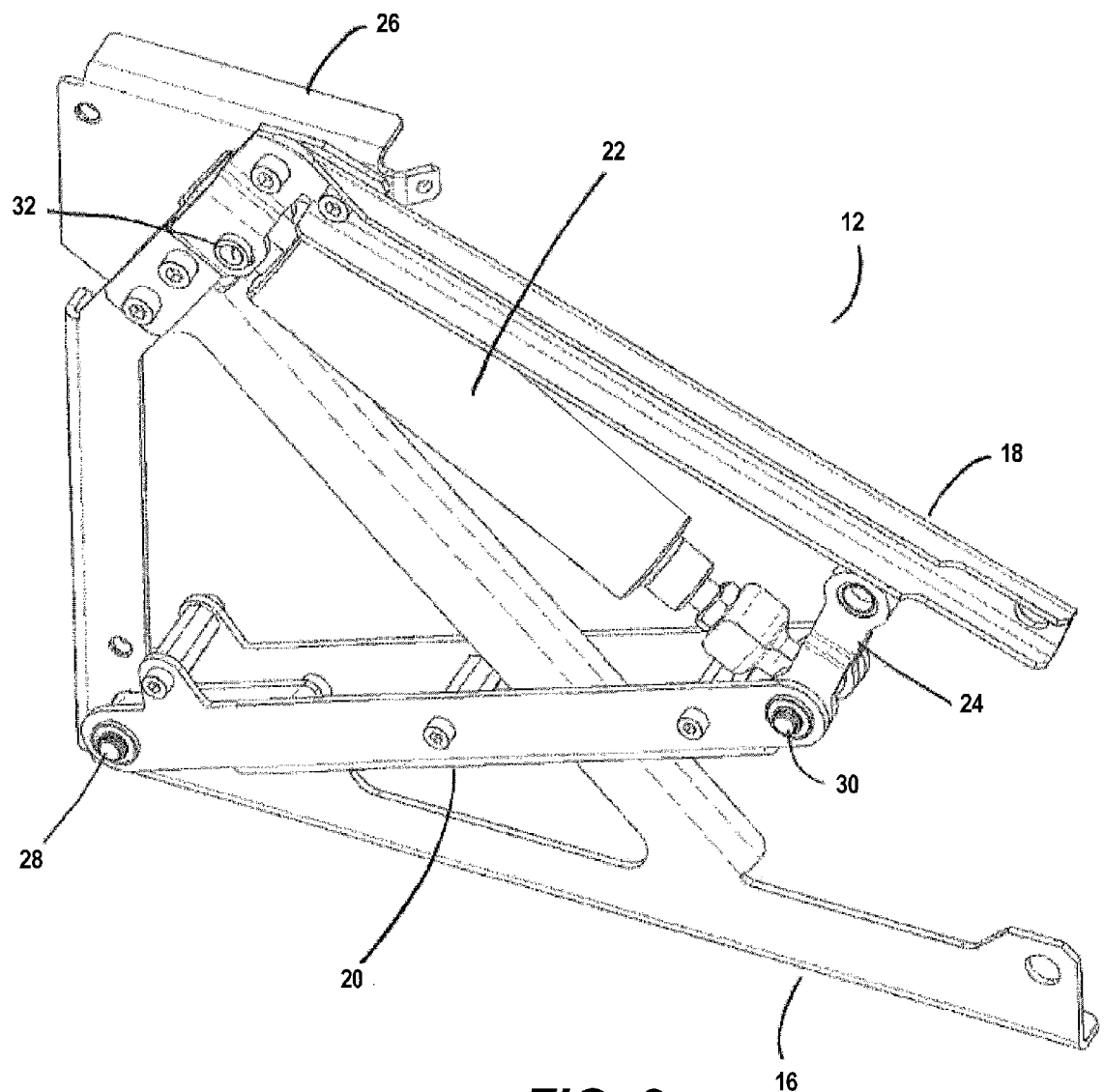
FIG. 2 is a front perspective view of a first embodiment of the actuator subassembly of the cassette clamping mechanism of the present invention.

As best seen in FIG. 1, cassette clamping mechanism 10 of the present invention generally includes actuator subassembly 12 and cassette receiving portion 14. Actuator subassembly 12 generally included lower bracket 16, upper bracket 18, reference link assembly 20, pneumatic cylinder 22 and transfer link 24. Upper bracket 18 and lower bracket 16 are connected at bracket stiffener 26 so as to hold brackets 16 and 18 rigidly together. Reference link 20 is pivotally attached to lower bracket 16 by shaft or pin 28. Cylinder 22 is pivotally attached to reference link 20 opposite pin 28 by pin 30. Pin 30 also pivotally attaches transfer link 24 to reference link 20. Cylinder 22 is pivotally attached to upper bracket 18 and lower bracket 16 at stiffener 26 opposite pin 30 by pin 32. Extension and retraction of cylinder 22, therefore, causes reference link 20 to pivot about pin 28, thereby raising and lowering transfer link 24.

Figure 3:
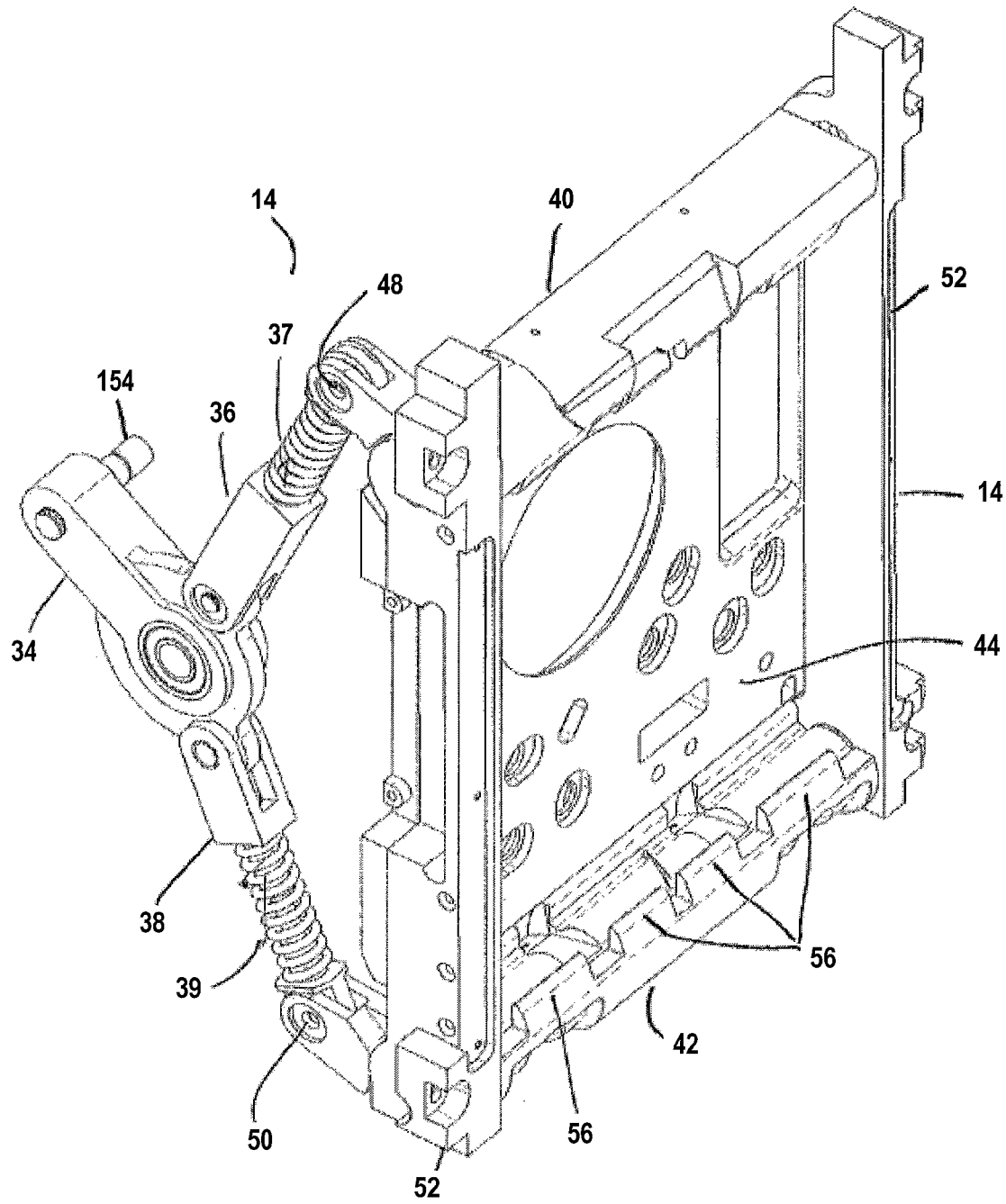
FIG. 3 is a front perspective view of the cassette receiving portion of the cassette clamping mechanism of the present invention.
Figure 4:
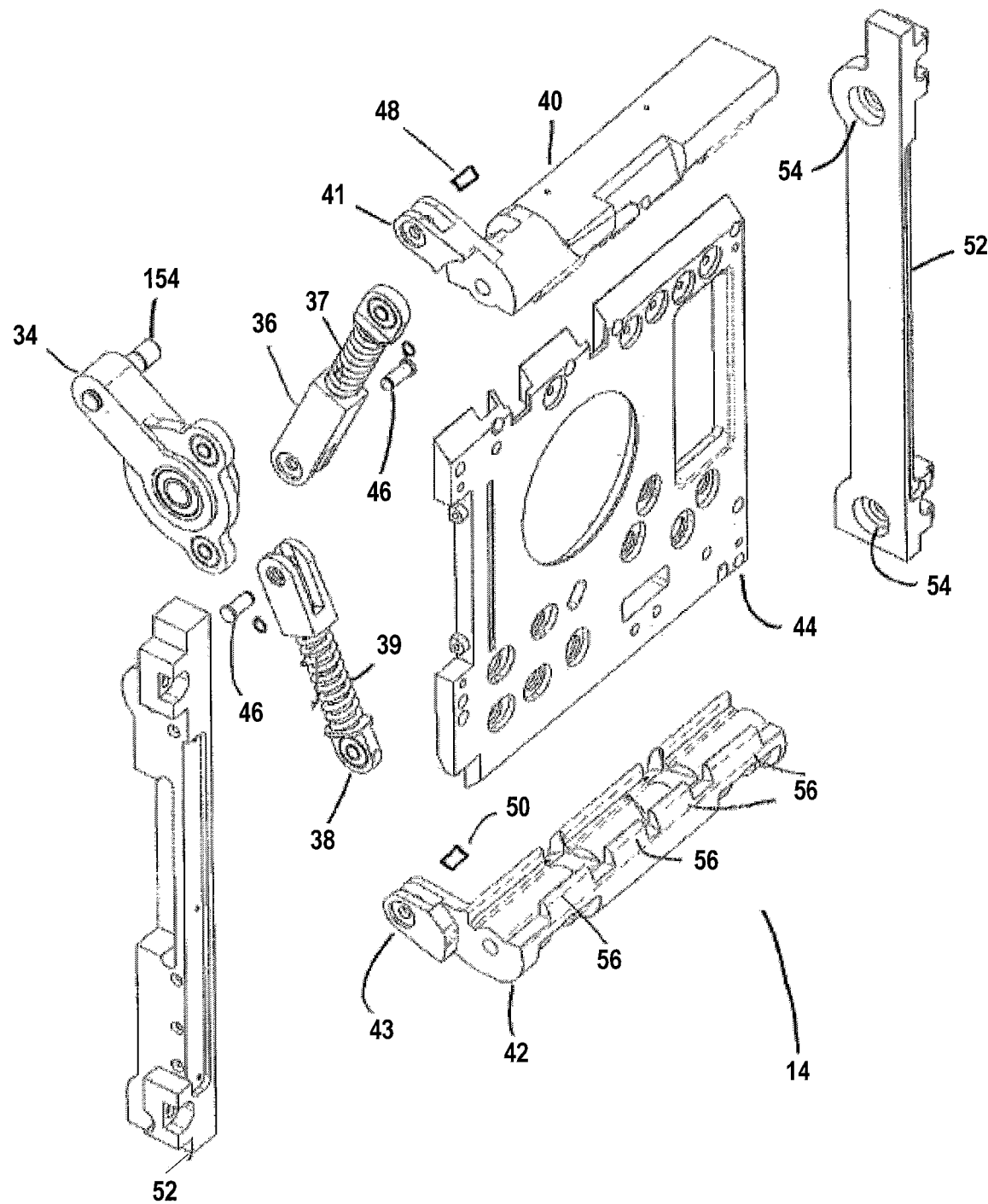
FIG. 4 is an exploded perspective view of the cassette receiving portion of the cassette clamping mechanism illustrated in FIG. 3.
Figure 5:
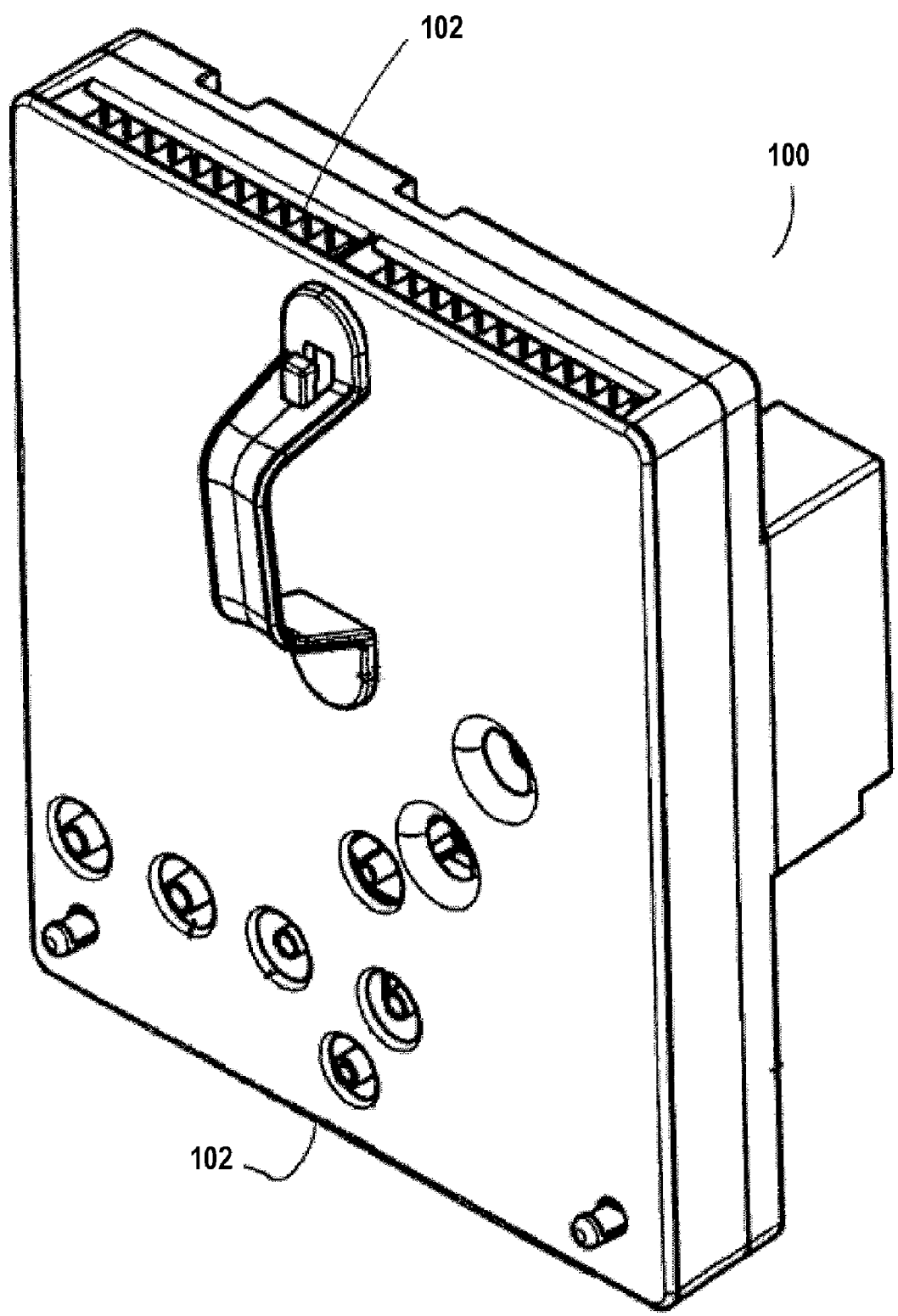
FIG. 5 is a front perspective view of a cassette that may be used with the clamping mechanism of the present invention.
Figure 6:
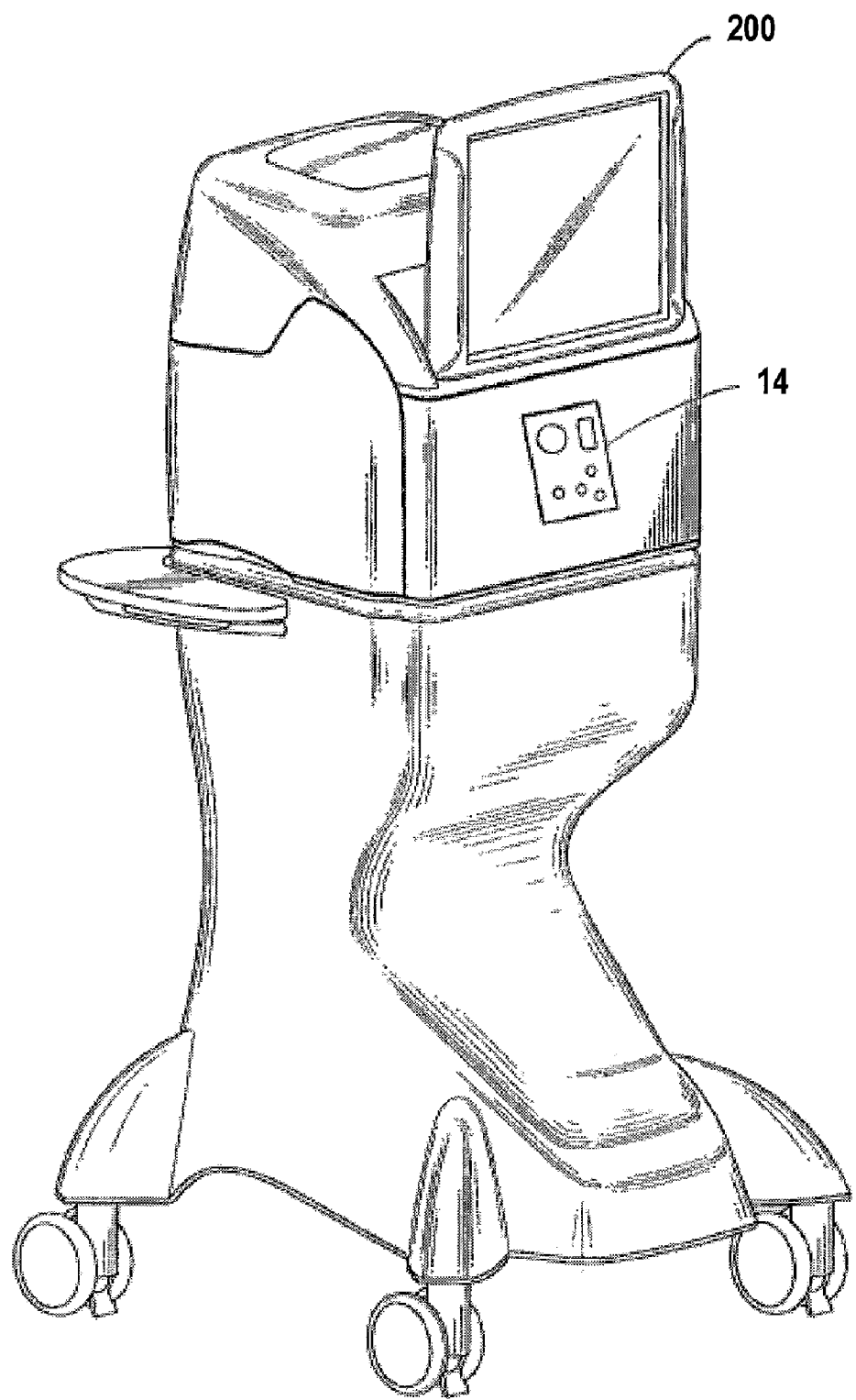
FIG. 6 is a front perspective view of a surgical console that may incorporate the cassette clamping mechanism assembly of the present invention.

As best seen in FIGS. 3, 4 and 6, cassette receiving portion 14 is externally exposed on surgical console 200 and generally consists of actuator wheel 34, upper link 36, lower link 38, upper clamp 40, lower clamp 42 and cassette faceplate 44. Upper link 36 and lower link 38 are connected to actuator wheel 34 by pins 46. Upper link 36 is connected to arm 41 on upper clamp 40 by pin 48 and lower link 38 is connected to arm 43 on lower clamp 42 by pin 50. Upper link 36 and lower link 38 contain intermediate springs 37 and 39, respectively that allow links 36 and 38 to compress and rebound. Such a construction allows for mechanism 10 to compensate for manufacturing variances in the construction of cassette 100 without causing damage to cassette 100. Upper clamp 40 and lower clamp 42 are assembled onto side rails 52 and pivot within holes 54 in side rails 52. The clamp/side rail subassembly is attached to cassette faceplate 44. So assembled, clockwise rotation of actuator wheel 34 pulls links 36 and 38 downward, causing upper clamp 40 to rotate clockwise and lower clamp 42 to rotate counter-clockwise. Counter-clockwise rotation of actuator wheel 34 pulls links 36 and 38 upward, causing upper clamp 40 to rotate counter-clockwise and lower clamp 42 to rotate clockwise. Actuator wheel 34 is connected to transfer link 24 by pin 154. The eccentric orientation of arms 41 and 43 result in an over-center rotation of clamps 40 and 42. Over-center rotation of clamps 40 and 42 result in clamps 40 and 42 being self-locking in the event of a loss of air pressure to cylinder 22.

In use, as described above, extension and retraction of cylinder 22 causes reference link 20 to pivot about pin 28, thereby raising and lowering transfer link 24. Raising and lowering transfer link 24 alternately causes clockwise and counter-clockwise rotation of actuator wheel 34, there by cause rotation and counter-rotation of upper clamp 40 and lower clamp 42. Upper clamp 40 and lower clamp 42 contain a plurality of clamping surfaces or fingers 56 that cooperate with clamping surfaces 102 on cassette 100. When cassette 100 is installed within cassette receiving portion 14 of mechanism 10, clockwise rotation of upper clamp 40 and counter-clockwise rotation of lower clamp 42 acts to draw the cassette into cassette receiving portion 14 and push the cassette against cassette faceplate 44, thereby firmly holding the cassette against faceplate 44.

Figure 7:
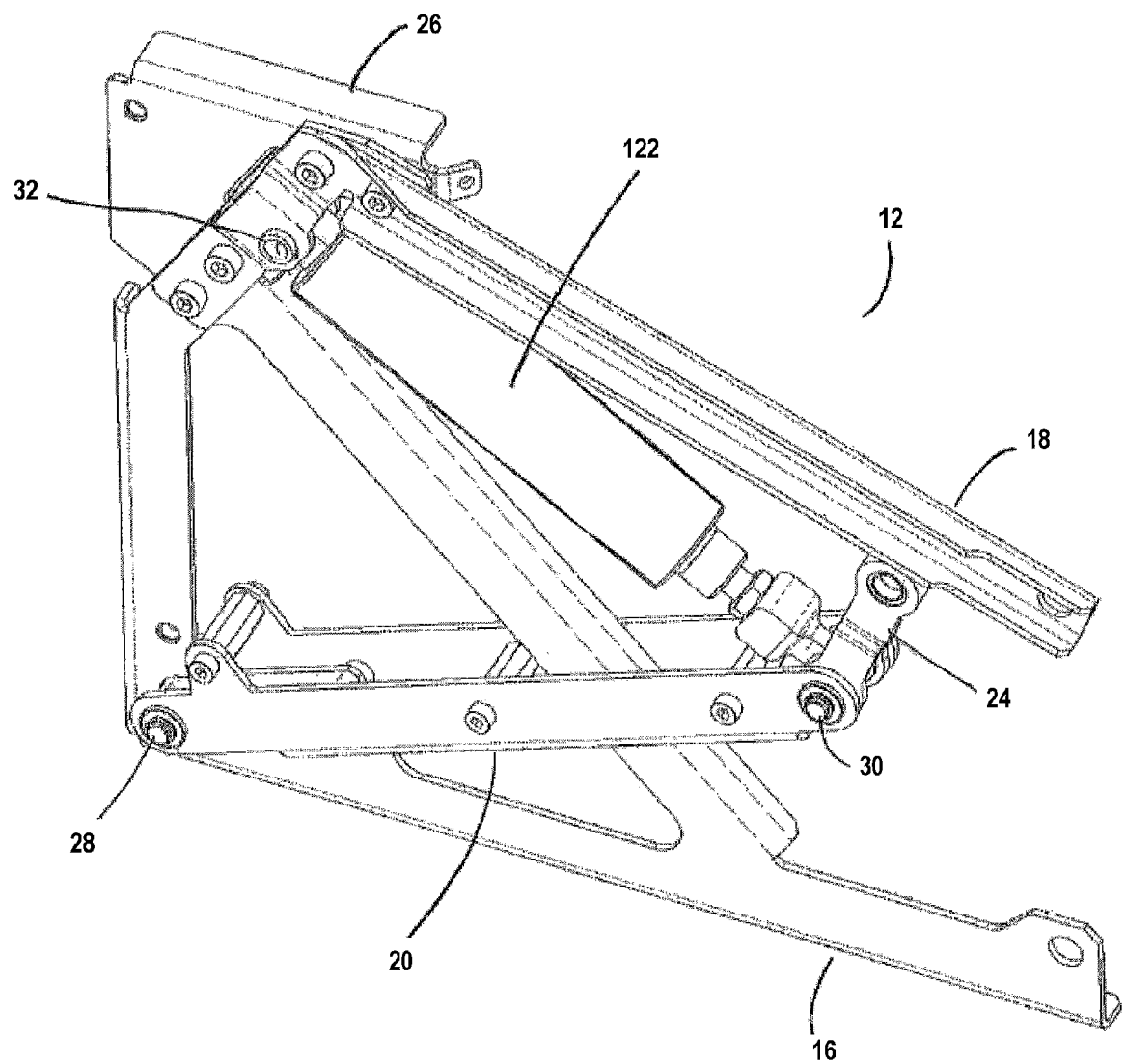
FIG. 7 is a front perspective view of a second embodiment of the actuator subassembly of the cassette clamping mechanism of the present invention.

As best seen in FIG. 7, in a second embodiment of the present invention, instead of a pneumatic device such as cylinder 22, movement of link 20 is caused by the operation of electromechanical device 122, such as a solenoid or an electric motor driven linear actuator.

This description is given for purposes of illustration and explanation. It will be apparent to those skilled in the relevant art that modifications may be made to the invention as herein described without departing from its scope or spirit.

We claim:

1. A cassette clamping mechanism, comprising:
   a frame;
   a pneumatic cylinder;
   a reference link pivotally mounted to the frame on a first end of the reference link and pivotally mounted to the pneumatic cylinder on a second end of the reference link so that extension and retraction of the pneumatic cylinder causes the reference link to pivot relative to the frame;
   an actuator wheel pivotally mounted to the second end of the reference link so that pivoting of the reference link causes rotation of the actuator wheel, wherein the actuator wheel is pivotally mounted to the reference link through a transfer link; and
   a pair of counter-rotating clamps attached to the actuator wheel;
   wherein the pneumatic cylinder is pivotally mounted to the frame on a first end of the pneumatic cylinder and to the reference link on a second end of the pneumatic cylinder, such that a clamping function of the pair of counter-rotating clamps occurs by extension of the pneumatic cylinder.

2. The clamping mechanism of claim 1 wherein each clamp is attached to the actuator wheel through a spring-loaded link.

3. The clamping mechanism of claim 1 wherein the pair of clamps are adapted to engage a cassette and wherein the pair of clamps are attached to the actuator wheel such that rotation of the actuator wheel causes the clamps to counter-rotate relative to each other.

4. A cassette clamping mechanism, comprising:
   a frame;
   an electric motor;
   a linear actuator configured to be driven by the electric motor;
   a reference link pivotally mounted to the frame on a first end of the reference link and pivotally mounted to the linear actuator on a second end of the reference link so that extension and retraction of the electric motor driven linear actuator causes the reference link to pivot relative to the frame;
   an actuator wheel pivotally mounted to the second end of the reference link so that pivoting of the reference link causes rotation of the actuator wheel, wherein the actuator wheel is pivotally mounted to the reference link through a transfer link; and
   a pair of counter-rotating clamps attached to the actuator wheel;
   wherein the linear actuator is pivotally mounted to the frame on a first end of the linear actuator and to the reference link on a second end of the linear actuator, such that a clamping function of the pair of counter-rotating clamps occurs by extension of the electric motor driven linear actuator.

5. The clamping mechanism of claim 4 wherein each clamp is attached to the actuator wheel through a spring-loaded link.

6. The clamping mechanism of claim 4 wherein the pair of clamps are adapted to engage a cassette and wherein the pair of clamps are attached to the actuator wheel such that rotation of the actuator wheel causes the clamps to counter-rotate relative to each other.

7. A cassette clamping mechanism, comprising:
   a frame;
   an actuator;
   a reference link pivotally mounted to the frame on a first end of the reference link and pivotally mounted to the actuator on a second end of the reference link so that extension and retraction of the actuator causes the reference link to pivot relative to the frame;
   an actuator wheel pivotally mounted to the second end of the reference link so that pivoting of the reference link causes rotation of the actuator wheel, wherein the actuator wheel is pivotally mounted to the reference link through a transfer link; and
   a pair of counter-rotating clamps attached to the actuator wheel;
   wherein the actuator is pivotally mounted to the frame on a first end of the actuator and to the reference link on a second end of the actuator, such that a clamping function of the pair of counter-rotating clamps occurs by extension of the actuator.

8. The clamping mechanism of claim 7, wherein the actuator is a solenoid.

9. The clamping mechanism of claim 7 wherein each clamp is attached to the actuator wheel through a spring-loaded link.

10. The clamping mechanism of claim 7 wherein the pair of clamps are adapted to engage a cassette and wherein the pair of clamps are attached to the actuator wheel such that rotation of the actuator wheel causes the clamps to counter-rotate relative to each other.

* * * * *